US009006283B2

(12) United States Patent
Krafft et al.

(10) Patent No.: US 9,006,283 B2
(45) Date of Patent: *Apr. 14, 2015

(54) METHODS OF MODIFYING AMYLOID β OLIGOMERS USING NON-PEPTIDIC COMPOUNDS

(75) Inventors: Grant A. Krafft, Glenview, IL (US); Todd Pray, San Mateo, CA (US); William F. Goure, Livermore, CA (US)

(73) Assignee: Acumen Pharmaceuticals, Inc., Livermore, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/777,264

(22) Filed: Jul. 12, 2007

(65) Prior Publication Data

US 2009/0018218 A1 Jan. 15, 2009

(51) Int. Cl.

| A61K 31/381 | (2006.01) |
|---|---|
| A61K 31/4155 | (2006.01) |
| A61K 9/20 | (2006.01) |
| A61K 9/00 | (2006.01) |
| A61K 9/02 | (2006.01) |
| A61K 9/14 | (2006.01) |
| A61K 31/41 | (2006.01) |
| A61K 31/415 | (2006.01) |
| C12N 5/0793 | (2010.01) |

(52) U.S. Cl.
CPC ............ *A61K 9/2054* (2013.01); *A61K 9/0019* (2013.01); *A61K 9/0075* (2013.01); *A61K 9/02* (2013.01); *A61K 9/146* (2013.01); *A61K 9/2059* (2013.01); *A61K 31/381* (2013.01); *A61K 31/41* (2013.01); *A61K 31/415* (2013.01); *C12N 5/0619* (2013.01); *C12N 2501/999* (2013.01)

(58) Field of Classification Search
CPC . A61K 31/381; A61K 31/415; C07D 207/30; C07D 241/04; C07D 333/22; C07D 333/54
USPC ......... 514/789, 438, 443, 447, 448, 403, 412, 514/423; 435/375; 530/300; 548/356.1, 548/358.1, 360.1; 549/29, 41, 43
See application file for complete search history.

(56) References Cited

U.S. PATENT DOCUMENTS

| 4,203,670 | A |   | 5/1980 | Bromberg |
|---|---|---|---|---|
| 4,420,568 | A |   | 12/1983 | Wang et al. |
| 4,429,230 | A |   | 1/1984 | Honkawa et al. |
| 4,476,229 | A |   | 10/1984 | Fino et al. |
| 4,510,251 | A |   | 4/1985 | Kirkemo et al. |
| 4,585,862 | A |   | 4/1986 | Wang et al. |
| 4,614,823 | A |   | 9/1986 | Kirkemo et al. |
| 4,668,640 | A |   | 5/1987 | Wang et al. |
| 4,681,859 | A |   | 7/1987 | Kramer |
| 4,686,085 | A | * | 8/1987 | Osterholm ...................... 422/45 |
| 4,751,190 | A |   | 6/1988 | Chiapetta et al. |
| 4,863,876 | A |   | 9/1989 | Hevey |
| 4,952,691 | A |   | 8/1990 | Wang et al. |
| 5,066,426 | A |   | 11/1991 | Wang et al. |
| 5,070,025 | A |   | 12/1991 | Klein et al. |
| 5,206,179 | A |   | 4/1993 | Ramsey |
| 5,315,015 | A |   | 5/1994 | Hui et al. |
| 5,391,740 | A |   | 2/1995 | Wang et al. |
| 5,407,834 | A |   | 4/1995 | Dubler et al. |
| 5,427,960 | A |   | 6/1995 | Wang et al. |
| 5,445,935 | A |   | 8/1995 | Royer |
| 5,661,035 | A |   | 8/1997 | Tsien et al. |
| 5,756,292 | A |   | 5/1998 | Royer |
| 5,804,395 | A |   | 9/1998 | Schade et al. |
| 5,914,245 | A |   | 6/1999 | Bylina et al. |
| 5,976,820 | A |   | 11/1999 | Jolley et al. |
| 5,981,200 | A |   | 11/1999 | Tsien et al. |
| 6,066,505 | A |   | 5/2000 | Cheng et al. |
| 6,171,807 | B1 |   | 1/2001 | Novitsky et al. |
| 6,197,928 | B1 |   | 3/2001 | Tsien et al. |
| 6,207,397 | B1 |   | 3/2001 | Lynch et al. |
| 6,218,506 | B1 |   | 4/2001 | Krafft et al. |
| 6,280,981 | B1 |   | 8/2001 | Dykens et al. |
| 6,284,544 | B1 |   | 9/2001 | Thompson et al. |
| 6,291,201 | B1 |   | 9/2001 | Garman |
| 6,294,330 | B1 |   | 9/2001 | Michnick et al. |
| 6,323,039 | B1 |   | 11/2001 | Dykens et al. |
| 6,326,142 | B1 |   | 12/2001 | Royer |
| 6,331,392 | B1 |   | 12/2001 | Laing et al. |
| 6,348,322 | B1 |   | 2/2002 | Strittmatter |
| 6,376,257 | B1 |   | 4/2002 | Persechini |
| 6,432,632 | B2 |   | 8/2002 | Nakayama et al. |

(Continued)

FOREIGN PATENT DOCUMENTS

| RU | 2280449 c2 | 4/2005 |
|---|---|---|
| RU | 2281766 C1 | 8/2006 |

(Continued)

OTHER PUBLICATIONS

U.S. Appl. No. 11/777,266, filed Jul. 12, 2007, Krafft.
International Search Report, PCT/US2007/073410, dated Aug. 4, 2008.
Doggrell, S.A., "A small-molecule lead compound for the treatment of Alzheimer's disease," Expert Opinion, Investig. Drugs, vol. 14, No. 2, 2005, pp. 199-201, XP002488991.
Roher, A.E. et al, "β-Amyloid-(1-42) is a major component of cerebrovascular amyloid deposits: Implications for the pathology of Alzheimer disease," Proceedings of the National Academy of Science, Washington, D.C., vol. 90, Nov. 1, 1993, pp. 10836-10840, XP002068754.
Roher, A.E. et al., "Morphology and Toxicity of Aβ-(1-42) Dimer Derived from Neuritic and Vascular Amyloid Deposits of Alzheimer's Disease," Journal of Biological Chemistry, American Cociety of Biolochemical Biologists, Birmingham, U.S., vol. 271, No. 34, Aug. 23, 1996, p. 20631-20635, XP002068753.

(Continued)

*Primary Examiner* — Sreeni Padmanabhan
*Assistant Examiner* — Sahar Javanmard
(74) *Attorney, Agent, or Firm* — Foley & Lardner LLP (57) ABSTRACT

Disclosed are methods of inhibiting, regulating, and/or modulating the formation of soluble, globular, non-fibrillar, neurotoxic amyloid $\beta_{1-42}$ oligomers from amyloid $\beta_{1-42}$ monomers. Also disclosed are methods of treating a patient suffering from diseases associated with the formation of soluble, globular, non-fibrillar, neurotoxic amyloid $\beta_{1-42}$ oligomers.

7 Claims, 2 Drawing Sheets

(56) References Cited

U.S. PATENT DOCUMENTS

| | | | |
|---|---|---|---|
| 6,448,018 B1 | 9/2002 | Nakayama et al. | |
| 6,456,734 B1 | 9/2002 | Youvan et al. | |
| 6,472,156 B1 | 10/2002 | Wittwer et al. | |
| 6,495,664 B1 | 12/2002 | Cubitt | |
| 6,511,815 B1 | 1/2003 | Burke et al. | |
| 6,515,113 B2 | 2/2003 | Raymond et al. | |
| 6,555,326 B1 | 4/2003 | Lustig et al. | |
| 6,569,628 B2 | 5/2003 | Laing et al. | |
| 6,596,546 B1 | 7/2003 | Jolley et al. | |
| 6,600,017 B1 | 7/2003 | Glabe et al. | |
| 6,630,295 B2 | 10/2003 | Mayer et al. | |
| 6,632,613 B1 | 10/2003 | Wei et al. | |
| 6,639,078 B1 | 10/2003 | Haffner et al. | |
| 6,642,001 B1 | 11/2003 | Bolk et al. | |
| 6,661,909 B2 | 12/2003 | Youvan et al. | |
| 6,689,574 B1 | 2/2004 | Cummings et al. | |
| 6,713,276 B2 | 3/2004 | Cordell et al. | |
| 6,762,280 B2 | 7/2004 | Schmidt et al. | |
| 6,770,448 B2 | 8/2004 | Glabe et al. | |
| 6,794,158 B2 | 9/2004 | Ingraham et al. | |
| 6,803,188 B1 | 10/2004 | Tsien et al. | |
| 6,824,990 B1 | 11/2004 | Blumer | |
| 6,828,106 B2 | 12/2004 | Colyer et al. | |
| 6,846,813 B2 | 1/2005 | Jagodzinska et al. | |
| 6,858,383 B2 | 2/2005 | Sabbadini | |
| 6,864,103 B2 | 3/2005 | Raymond et al. | |
| 6,864,290 B2 | 3/2005 | Schostarez et al. | |
| 6,881,546 B2 | 4/2005 | Sabbadini | |
| 6,905,827 B2 | 6/2005 | Wohlgemuth et al. | |
| 6,906,104 B2 | 6/2005 | Schostarez et al. | |
| 6,908,769 B2 | 6/2005 | Belik et al. | |
| 6,927,401 B1 | 8/2005 | Palo | |
| 7,666,908 B2 | 2/2010 | Pomytkin et al. | |
| 2006/0178302 A1 | 8/2006 | Krafft et al. | |
| 2006/0189582 A1* | 8/2006 | McLaurin | 514/129 |
| 2007/0037752 A1 | 2/2007 | Ansorge et al. | |
| 2007/0048312 A1 | 3/2007 | Klein et al. | |
| 2007/0218499 A1 | 9/2007 | Lambert et al. | |
| 2008/0300205 A1 | 12/2008 | Tsai et al. | |
| 2011/0098309 A1 | 4/2011 | Look et al. | |

FOREIGN PATENT DOCUMENTS

| | | |
|---|---|---|
| WO | WO 01/55093 | 8/2001 |
| WO | WO 02/32896 | 4/2002 |
| WO | WO-03/082270 | 10/2003 |
| WO | WO 03/104437 | 12/2003 |
| WO | WO 2004/031400 | 4/2004 |
| WO | WO 2005/034940 | 4/2005 |
| WO | WO 2005/037257 | 4/2005 |
| WO | WO 2005/116640 | 12/2005 |
| WO | WO 2006/014478 | 2/2006 |
| WO | WO 2006/055178 | 5/2006 |
| WO | PCT/US2007/073408 | 7/2007 |
| WO | WO 2007/134449 | 11/2007 |
| WO | PCT/US2007/073410 | 7/2008 |

OTHER PUBLICATIONS

U.S. Appl. No. 11/777,266, filed Jul. 12, 2007, Krafft et al.
Acumen Pharmaceuticals (2006) "Developing disease-modifying drugs that block and reverse memory loss in Alzheimer's disease" Science Update SFN Reception—Oct. 14, 2006 Atlanta, GA—Presentation.
Acumen Pharmaceuticals (2006) "New Alzheimer's disease therapeutics: Preventing ADDL compromise of synaptic signaling" Neurodegenerative Diseases: Biology and Therapeutics: Cold Spring Harbor, New York, Nov. 30-Dec. 3, 2006—Presentation.
De Felice et al. (2001) "Inhibition of Alzheimer's disease β-amyloid aggregation, neurotoxicity, and in vivo deposition by nitrophenols: implications for Alzheimer's therapy" FASEB J. Published online Mar. 20, 2001.
De Felice et al. (2004) "Targeting the neurotoxic species in Alzheimer's disease: inhibitors of Aβ oligomerization" FASEB J. 18:1366-1372.
Fulop et al. (2004) "β-Amyloid pentapeptide RIIGL$_a$ inhibits Aβ$_{1-42}$ aggregation and toxicity" Biochem. Biophys. Res. Commun. 324:64-69.
Gervais (2004) "GAG Memetics: Potential to Modify Underlying disease Process in AD" Neuirobiol. Aging 25:S11-12.
Goure et al. (2007) "Development of novel, ADDL-targeting, disease modifying therapeutics for the treatment Alzheimer's disease" 8$^{th}$ International AD-PD Conference Mar. 14-18, 2007—Abstract.
Goure et al. (2007) "Development of novel, ADDL-targeting, disease modifying therapeutics for the treatment Alzheimer's disease" 8$^{th}$ International AD-PD Conference Mar. 14-18, 2007—Poster.
Goure et al. (2007) "Preclinical development of disease modifying therapeutics for the treatment Alzheimer's disease" Alzheimer's Disease International Conference—Jun. 9-12, 2007—Abstract.
Goure et al. (2007) "Preclinical development of disease modifying therapeutics for the treatment Alzheimer's disease" Alzheimer's Disease International Conference—Jun. 9-12, 2007—Poster.
Krafft (2007) "Stable trimeric Aβ peptides: Potential vaccine immunogens to prevent ADDL-triggered memory deficits" Alzheimer's Disease: From Molecular Mechanisms to Drug Discover Apr. 18, 2007 Punta Cana, Dominican Republic—Presentation.
Krafft et al. (2006) "Discovery of ADDL-targeting small molecule drugs for Alzheimer's disease" ICAD Jul. 15-20, 2006 Poster.
Lecanu et al. (2004) "Identification of naturally occurring spirostenols preventing β-amyloid-induced neurotoxicity" Steroids 69:1-16.
Liu et al. (2005) "Trehalose differentially inhibits aggregation and neurotoxicity of beta-amyloid 40 and 42" Neurobiol. Disease 20:74-81.
Maezawa et al. (2006) "A novel tricyclic pyrone compound ameliorates cell death associated with intracellular amyloid-β oligomeric complexes" J. Neurochem. 98:57-67.
McGovern et al. (2002) "A Common Mechanism Underlying Promiscuous Inhibitors from Virtual and High-Throughput Screening" J. Med. Chem. 45:1712-1722.
McLaurin et al. (2006) "Cyclohexanehexol inhibitors of Aβ aggregation prevent and reverse Alzheimer phenotype in a mouse model" Nature Med. 12:801-808.
Necula et al. (2007) "Small Molecule inhibitors of Aggregation indicate that Amyloid β Oligomerization and Fibrillization Pathways are Independent and Distinct" J. Biol. Chem. 282(14):10311-10324.
Oprea et al. (2001) "Is ther a difference between Leads and Drugs? A Historical Perspective" J. Chem. Inf. Comput. Sci. 41:1308-1315.
Pray et al. (2006) "A homogenous fluorescence assay of ADDL assembly and anti-ADDL antibody properties" Neuroscience 36$^{th}$ Annual meeting Oct. 14-18, 2006 Atlanta, GA—Abstract.
Pray et al. (2006) "A homogenous fluorescence assay of ADDL assembly: Inhibition by biologics & small molecules" Neuroscience 36$^{th}$ Annual meeting Oct. 14-18, 2006 Atlanta, GA—Presentation.
Ritchie et al. (2003) "Metal-Protein Attenuation with Iodochlorhydrozyquin (Clioguinol) Targeting Aβ Amyloid Deposition and Toxicity in Alzheimer Disease" Arch. Neurol. 60:1685-1691.
Roche et al. (2002) "Development of Virtual screening Method for Identification of "Frequent Hitters" in Compound Libraries" J. Med. Chem. 45:137-142.
Wang et al. (2002) "Soluble oligomers of β amyloid (1-42) inhibit long-term potentiation but not long-term depression in rat dentate gyrus" *Brain Research* 924:133-140.
Yang et al. (2005) "Curcumin Inhibits Formation of Amyloid β Oligomers and Fibrils, Binds Plaques, and Reduces Amyloid in Vivo" J. Biol. Chem. 280(7):5892-5901.
Yao et al. (2001) "The Ginkgo biloba extract EGb 761 rescues the PC12 neuronal cells from β-amyloid-induced cell death by inhibiting the formation of β-amyloid-derived diffusible neurotoxic ligands" Brain Res. 889:181-190.
Yu et al. (2002) "Per-6-Substituted β-cyclodextrin Libraries Inhibit Formation of β-Amyloid-Peptide (Aβ)-Derived, Soluble Oligomers" J. Mol. Neurosci. 19:51-55.
Blennow et. al. (2006), "Alzheimer's disease," Seminar, Clinical Neurochemistry Laboratory, Dept. of Neuroscience and Physiology, vol. 368:387-403.

(56) References Cited

OTHER PUBLICATIONS

International Search Report, PCT/2008/069878, dated Jan. 28, 2009.
Catalano, S. et al., "The Role of Amyloid-Beta Derived Diffusible Ligands (ADDLs) in Alzheimer's Disease," Current Topics in Medicinal Chenmistry, Bentham Science Publishers, Hilversum, NL, vol. 6, Jan. 1, 2006, pp. 597-608, XP002494511.
Look, G. et al., "Discovery of ADDL-targeting small molecule drugs for Alzheimer's disease," Current Alzheimer Research, vol. 4, No. 5, Dec. 1, 2007, pp. 562-567, XP009102895.
Belikov, V.G., "Pharmaceutical Chemistry," Moscow, Vyshaya Shkola Publishing House, (1993), 43-46 (In Russian—English translation not available).
Kharkevich, D.A., "Pharmacology," Moscow, Medicina Publishing House, (1987), 47-48 (In Russian—English translation not available).
Russian 2nd Office Action and translation dated Jan. 26, 2013 in related Russian Patent Application No. 2010104039.
Sergeev, P.V., "Concise course in the molecular pharmacology," Moscow, (1975), 10-11 (In Russian—English translation not available).
Afonso A M et al: "Pyrocatechol-1-Aldehyde Salicyloylhydrazone as Reagent for the Spectrofluorimetric Determination of Zinc", Mikrochimica Acta, Springer Verlag, Vienna, AT, vol. 2, Jan. 1, 1984, pp. 53-60, XP008017272.
Anonymous: "1,2,3-Thiadiazole-5-carboxylic acid, 4-mthyl-, 2-[(5-chloro-2-hydroxyphenyl)methylene]hydraz ide", Registry,, May 11, 2006, XP007919802.
Anonymous: "Benzoic acid, 2-hydroxy-, 2-(3-amino-1-methyl-3-oxopropylidene)hydrazide", Registry,, Aug. 1, 2001, XP007919799.
Anonymous: "Benzoic acid, 2-hydroxy-, 2-[ (2-hydroxy-3-methylphenyl)methylene]hyd razide", Registry,, Apr. 3, 2006, XP007919801.
Anonymous: "Benzoic acid, 2-hydroxy-, 2-[(3-bromo-5-chloro-2-hydroxyphenyl)methylene]hydrazide", Registry,, Mar. 26, 2001, XP007919797.
Anonymous: "Benzoic acid, 2-hydroxy-, 2-[(5-chloro-2-hydroxy-3-methoxyphenyl)methylene]hydrazide", Registry,, Mar. 26, 2001, XP007919796.
Anonymous: "Benzoic acid, 2-hydroxy-, 2-[[4-(diethylamino)-2-hydroxyphenyl]methylene]hydrazide", Registry,, Jan. 23, 2001, XP007919795.
Anonymous: "Benzoic acid, 2-hydroxy-5-nitro-,2-[ (2-hydroxy-5-methoxyphenyl) methylene]hydrazide", Registry,, Jun. 11, 2003, XP007919800.
Anonymous: "Benzoic acid, 4-nitro-, 2-[3-oxo-3-(2-thienyl)-1-(trifluoromethyl)propylidene]hydrazide", Registry,, Jul. 18, 2001, XP007919798.
Anonymous: "Benzoic acid, 5-bromo-2-hydroxy-, 2-[(2-hydroxy-5-methoxyphenyl)methylene]hydrazide", Registry,, Mar. 4, 1998, XP007919794.
Cooke et al., "Plasticity in the human central nervous system", Brain (2006) 129, 1659-1673.
Kholodov et al., "The clinical pharmakinetics", Meditsina, 1985, pp. 83-380.
Lacor et al. "Synaptic Targeting by Alzheimer's-Related Amyloid Beta Oligomers",(2004) J. Neurosci. 24(45):10191-10200.
Lambert et al. "diffusible, nonfibrillar ligands derived from ABeta1-42 are potent central nervous system neurotoxins", (1998) Proc. Natl. Acad. Sci. USA 95:6448-6453.
Ma T S et al: "Antituberculous activity of hydrazine derivatives of phenolic acids and aldehydes", Antibiotics and Chemotherapy, Antibiotics and Chemotherapy, Northfield, IL, US, vol. 3, Jan. 1, 1953, pp. 491-494, XP009154364.
Mohan M et al: "Synthesis, Characterization and Antitumor Activity of Some Metal Complexes of 3- and 5-Substituted Salicylaldehyde O-Hydroxybenzoylhydrazones", Inorganica Chimica Acta, Elsevier BV, NL, vol. 152, No. 1, Jan. 1, 1988, pp. 25-36, XP008038629.
Sergeev, "The Brief Course on Molecular Pharmacology", 1975, p. 10.
Syamal A et al: "Bromate-Bromide Mixture As a Titrimetric Reagent for the Determination of Some Ortho-Hydroxyaldehydes, Acids, Hydrazides, Schiff Bases and Their Metal Complexes", Journal of the Indian Chemical Society, The Indian Chemical Society, Calcutta; IN, vol. 65, Feb. 1, 1988, pp. 112-116, XP002067541.
Terletskaya A V et al: "Chemiluminescence of some acyclic hydrazides in chlorine oxidation", Ukrainskii Khimicheskii Zhurnal, Neorhanichnoyi Khimii Im. V.I.Vernadskoho, Kyiv, UA, vol. 45, No. 12, Jan. 1, 1979, pp. 1227-1233, XP009154368.
Georganopoulou, et al., "Nanoparticle-based detection in cerebral spinal fluid of a soluble pathogenic biomarker for Alzheimer's disease", PNAS, The National Academy for the Sciences of the USA (2005) vol. 102: No. 7, pp. 2273-2276.
Chang et al., "Femtomole immunodetection of synthetic and endogenous amyloid-beta oligomers and its application to Alzheimer's disease drug candidate screening," J. Mol. Neurosci., (2003), 20:305-313.
Gabathuler R., "Approaches to transport therapeutic drugs across the blood-brain barrier to treat brain diseases," Neurobio. Disease, (2010), 37:48-57.
Kurihara et al., "Aβ1-40 Peptide Radiopharmaceuticals for Brain Amyloid Imaging: 111In Chelation, Conjugation to Poly(ethylene glycol)-Biotin Linkers, and Autoradiography with Alzheimer's Disease Brain Sections," Bioconjuqate Chem., (2000), 11:380-386.

\* cited by examiner

METHODS OF MODIFYING AMYLOID β OLIGOMERS USING NON-PEPTIDIC COMPOUNDS

BACKGROUND OF THE INVENTION

1. Field of the Invention

This invention relates to methods of inhibiting, regulating, and/or modulating the formation of soluble, globular, non-fibrillar, neurotoxic amyloid $\beta_{1-42}$ oligomers from amyloid $\beta_{1-42}$ monomers using non-peptidic compounds having a molecular weight of less than 1000. This invention also relates to methods of treating a patient suffering from diseases associated with the formation of soluble, globular, non-fibrillar, neurotoxic amyloid $\beta_{1-42}$ oligomers by administering non-peptidic compounds to the patients.

2. State of the Art

Alzheimer's disease (AD) is a fatal progressive dementia that has no cure at present. Although the molecular basis of the disease is not established, considerable evidence now implicates neurotoxins derived from amyloid beta (Aβ) peptides and in particular the 42-amino acid amyloid beta peptide (A$\beta_{1-42}$). Aβ is an amphipathic peptide, the abundance of which is increased by gene mutations and risk factors linked to AD. Fibrils formed from Aβ constitute the cores of amyloid senile plaques, which are hallmarks of AD brain. Analogous fibrils generated in vitro are lethal to cultured brain neurons. These findings provided the central rationale for the original amyloid cascade hypothesis, a theory in which memory loss was proposed to be the consequence of neuron death caused by fibrillar Aβ (Hardy and Higgins (1992) Science 256:184-185).

Despite its strong experimental support and intuitive appeal, the original amyloid cascade hypothesis has proven inconsistent with key observations, including the poor correlation between dementia and amyloid senile plaque burden (Katzman (1988) Ann. Neurol. 23(2):138-144). Using a transgenic mouse model of AD, two surprising findings were obtained when the mice were treated with monoclonal antibodies against Aβ: (1) vaccinated mice showed reversal of memory loss, with recovery evident in 24 hours; and (2) cognitive benefits of vaccination accrued despite no change in senile plaque levels (Dodart et al. (2002) Nat. Neurosci 5:452-457; Kotilinek et al. (2002) J. Neurosci. 22:6331-6335). Such findings are not consistent with a mechanism for memory loss dependent on neuron death caused by amyloid fibrils.

Salient flaws in the original amyloid cascade hypothesis have been eliminated by an updated amyloid cascade hypothesis that incorporates a role for additional neurologically active molecules formed by Aβ self-assembly. These molecules are amyloid β-derived diffusible ligands (ADDLs), which assemble from A$\beta_{1-42}$ at low concentrations (Lambert et al. (1998) Proc. Natl. Acad. Sci. USA 95:6448-6453). Essentially the missing links in the original amyloid cascade hypothesis, ADDLs rapidly inhibit long term potentiation (Lambert et al. (1998) Proc. Natl. Acad. Sci. USA 95:6448-6453; Walsh et al. (2002) Nature 416: 535-539; Wang et al. (2002) Brain Res. 924:133-140), a classic experimental paradigm for memory and synaptic plasticity. In the updated Aβ cascade hypothesis memory loss stems from synapse failure, prior to neuron death, with failure being caused by ADDLs, not fibrils (Hardy and Selkoe (2002) Science 297:353-356). ADDLs occur in brain tissue and are strikingly elevated in AD brain tissue compared to age matched controls (Kayed et al. (2002) Science 300:486-489; Gong et al. (2003) Proc. Natl. Acad. Sci. USA 100:10417-10422) and in AD transgenic mice models (Kotilinek et al. (2002) J. Neurosci. 22:6331-6335; Chang et al. (2003) J. Mol. Neurosci. 20:305-313).

A simplistic mechanistic approach to this theory can be illustrated as follows:

where formation of ADDLs is a separate pathway from formation of amyloid senile plaque both of which are in equilibrium with monomeric A$\beta_{1-42}$.

Further experiments have shown important neurological properties of ADDLs. ADDLs were shown to have selective toxicity to hippocampal CA1 neurons compared with CA3 neurons, and the complete absence of toxicity towards cerebellar neurons (Kim et al. (2003) FASEB J. 17:118-120). Ventricular injection of A$\beta_{1-42}$ oligomers into wild-type rats resulted in rapid, compromised behavioral models with complete recovery occurring within 24 hours (Cleary et al. (2005) Nat. Neurosci. 8:79-84) and these deficits are attributed to higher order oligomers, specifically 12-mer oligomers (Lesne et al. (2006) Nature 440:352-357). ADDL binding to neurons occurs with high specificity and is localized to post-synaptic receptors on a subset of hippocampal neurons (Lacor et al. (2004) J. Neurosci. 24:10191-10200). This triggers the rapid and persistent up-regulation of the immediate early gene product arc, translation of which is activity dependent at polyribosomes localized to subsets of dendritic spines (Steward et al. (1998) Neuron 21:741-751; Guzowski et al. (2000) J. Neurosci. 20:3993-4001). More recently, ADDLs have been implicated as upstream activators of tau phosphorylation and have been shown to interfere with animal behavior at femtomolar levels (Matsubara et al. (2004) Neurobiol. Aging 25:833-841).

The reversibility of memory loss in mouse models, coupled with the neurological properties of ADDLs and their presence in an AD brain, provides strong support for the hypothesis that AD is a disease of ADDL-induced synaptic failure (Lambert et al. (1998) Proc. Natl. Acad. Sci. USA 95:6448-6453; Klein et al. (2001) Trends Neuroscis. 24:219-220; Selkoe (2002) Science 298:789-791).

The use of antibodies specific to ADDLs is a powerful way to modulate the equilibrium between monomeric A$\beta_{1-42}$ and ADDLs thereby providing treatment for disease conditions mediated by ADDLs. However, antibody delivery is typically limited to injectable solutions which pose patient compliance issues as well as the presence of an attending clinician. Small molecules that modulate this equilibrium, deliverable by non-injectable means such as oral delivery, transdermal delivery, pulmonary delivery, nasal delivery, etc. would be particularly beneficial.

A number of small molecules developed originally as amyloid fibril blockers are purported to possess Aβ oligomer assembly blocking properties. Some of these compounds include Alzhemd™ (Gervais (2004) Neuirobiol. Aging 25:S11-12), Clioquinol (Ritchie et al. (2003) Arch. Neurol. 60:1685-1691), substituted β-cyclodextrins (Yu et al. (2002) J. Mol. Neurosci. 19:51-55), trehalose (Lui (2005) Neurobiol. Disease 20:74-81), simple amino, carbonyl, and nitro substituted phenols (De Felice et al. (2001) FASEB J. March 20; De Felice et al. (2004) FASEB J. 18:1366-1372), Curcumin (Yang et al. (2005) J. Biol. Chem. 280(7):5892-5901), cyclohexanehexol analogs (McLaurin et al. (2006) Nature Med. 12:801-808), spirosterols (Lecanu et al. (2004) Steroids 69:1-16) and tricyclic pyrones (Maeqawa et al. (2006) J. Neurochem. 98:57-67). Two of these compounds, Alzhemd™ and Clioquinol, have progressed into clinical trials.

Alzhemed™ (3-amino-1-propanesulfonic acid), a so-called "GAG mimetic," is proposed to reduce soluble and insoluble amyloid levels by binding to Aβ monomer, although no experimental details have appeared to confirm the proposed mode of action. Alzhemed™ has recently completed a 20 month open-label extension of a Phase II trial, and there are reports of slowed cognitive decline in some patients with mild AD, however, no efficacy was observed during the blinded phase of the study (Gervais (2004) Neuirobiol. Aging 25:S11-12).

The second compound in a phase II clinical trial, Clioquinol, was shown to stabilize the patients' cognitive ability compared to untreated patients and showed lower $A\beta_{1-42}$ levels in their plasma (Ritchie et al. (2003) Arch. Neurol. 60:1685-1691). However, a toxic impurity (a di-iodo form of Clioquinol) made during production has resulted in the study being halted and Clioquinol being replaced with an analog termed PBT2 (Blennow et al. (2006) Lancet 368:387-403).

Lastly, an unidentified compound or compounds from an extract of ginko biloba leaves was reported to lower the levels of $A\beta_{1-42}$ trimers and tetramers and increase the levels of high molecular weight polymers in a dose dependent manner (Yao et al. (2001) Brain Res. 889:181-190). Dose dependent protection against Aβ oligomer induced toxicity to PC-12 cells was also reported.

Of the compounds reported to block Aβ assembly or bind to $A\beta_{1-42}$ monomer, few appear to have high therapeutic potential. Given its very simple structure and hydrophilic properties, it is highly unlikely that Alzhemed™ has high and selective affinity for $A\beta_{1-42}$ monomer. Any effect that Alzhemed™ has on Aβ aggregation or disaggregation is likely attributable to its interaction with ionic residues near the N-terminus of $A\beta_{1-42}$. The cyclodextrins do not have either lead-like or drug-like properties that would recommend them for development (Oprea et al. (2001) J. Chem. Inf. Comput. Sci. 41:1308-1315; Vieth et al. (2004) J. Med. Chem. 47:224-232), and the phenols of De Felice contain aldehyde and nitro functionalities that are often considered reactive and excluded from screening libraries (Walters and Namchuk (2003) Nat. Rev. 2:259-266). A number of molecules containing the phenol functionality have been reported as "frequent hitters" in screening libraries (Roche et al. (2002) J. Med. Chem. 45:137-142). Thus, further evaluation of the activity and selectivity of the phenols of De Felice is needed to confirm that these compounds are valid hits. Some compounds with a steroidal backbone have been reported to be promiscuous inhibitors due to an unexpected self aggregation process (McGovern et al. (2002) J. Med. Chem. 45:1712-1722), which may explain the ambiguous spirosterol results. Finally, the active ingredient in the ginko biloba extract is unknown. Thus, most of the purported Aβ assembly blockers would not be considered compounds for therapeutic development.

Notwithstanding these putative results and as noted above, binding assays indicate that these compounds are, at best, moderate antagonists to ADDL formation.

Accordingly, it would be particularly beneficial to provide for small molecules which provide enhanced inhibition, regulation, and/or modulation of ADDL formation.

SUMMARY OF THE INVENTION

This invention is directed to the discovery that soluble, globular, non-fibrillar, neurotoxic $A\beta_{1-42}$ (ADDL) formation can be antagonized by substantially pure non-peptidic compounds having a molecular weight of less than 1500, preferably less than 1000, which compounds antagonize ADDL formation at levels higher than those previously achievable. This invention is further directed to the discovery of numerous scaffolds which exhibit this enhanced antagonism evidencing that it is not scaffold-dependent.

Accordingly, in one of its method aspects, this invention is directed to a method for antagonizing neurotoxic ADDL formation from monomeric $A\beta_{1-42}$ by contacting monomeric $A\beta_{1-42}$ with a substantially pure non-peptidic compound, said compound being characterized by:
  (a) having a molecular weight of less than 1000;
  (b) being an antagonist against formation of neurotoxic ADDLs from $A\beta_{1-42}$ monomers; and
  (c) exhibiting an $IC_{50}$ of about 5 μM or less in the assay of Example 1, which measures the formation of neurotoxic ADDLs.

In yet another embodiment, the invention is directed to a method of inhibiting, regulating and/or modulating the ADDL-induced neuronal dysfunction and/or neurotoxicity in a neuronal cell by inhibiting the formation of ADDLs. The method comprises contacting $A\beta_{1-42}$ monomers which may be in the presence of neuronal cells with an effective amount of a substantially pure non-peptidic compound, said compound being characterized by:
  (a) having a molecular weight of less than 1000;
  (b) being an antagonist against formation of neurotoxic ADDLs from $A\beta_{1-42}$ monomers; and
  (c) exhibiting an $IC_{50}$ of about 5 μM or less in the assay of Example 1, which measures the formation of neurotoxic ADDLs.

In another embodiment, the invention is directed to a method for inhibiting oligomerization or further oligomerization of monomeric $A\beta_{1-42}$ into neurotoxic ADDLs which method comprises contacting monomeric $A\beta_{1-42}$ with an effective amount of a substantially pure non-peptidic compound, said compound being characterized by:
  (a) having a molecular weight of less than 1000;
  (b) being an antagonist against formation of neurotoxic ADDLs from $A\beta_{1-42}$ monomers; and
  (c) exhibiting an $IC_{50}$ of about 5 μM or less in the assay of Example 1, which measures the formation of neurotoxic ADDLs.

In another embodiment, the invention is directed to a method of inhibiting, regulating and/or modulating ADDL formation or the activity of such ligand in a patient suffering from or at risk from suffering from a disease associated with the formation of $A\beta_{1-42}$ oligomers. The method comprises administering to the patient a therapeutically effective amount of a substantially pure non-peptidic compound, said compound being characterized by:
  (a) having a molecular weight of less than 1000;
  (b) being an antagonist against formation of neurotoxic ADDLs from $A\beta_{1-42}$ monomers; and
  (c) exhibiting an $IC_{50}$ of about 5 μM or less in the assay of Example 1, which measures the formation of neurotoxic ADDLs.

In yet another embodiment, the invention is directed to a method for treating a patient suffering from or at risk of suffering from an ADDL-related disease selected from the group consisting of Alzheimer's disease, Down's Syndrome, stroke, mild cognitive impairment, focal ischemia associated dementia, and neuronal degeneration. The method comprises administering to said patient a therapeutically effective amount of a substantially pure non-peptidic compound, said compound being characterized by:
- (a) having a molecular weight of less than 1000;
- (b) being an antagonist against formation of neurotoxic ADDLs from $A\beta_{1-42}$ monomers; and
- (c) exhibiting an $IC_{50}$ of about 5 µM or less in the assay of Example 1, which measures the formation of neurotoxic ADDLs.

In some embodiments of the invention, the compounds have a molecular weight of less than 1500. In other embodiments, the compounds are characterized in that they exhibit an inhibition in the formation of neurotoxic ADDLs as measured by an $IC_{50}$ of about 2 µM or less in the assay of Example 1 and, more preferably, 1 µM or less.

In another embodiment, the present invention relates to a composition for use in the treatment of a patient suffering from or at risk of suffering from a disease selected from the group consisting of Alzheimer's disease, Down's Syndrome, stroke, mild cognitive impairment, focal ischemia associated dementia, and neuronal degeneration wherein the composition comprises a therapeutically effective amount of a substantially pure non-peptidic compound, said compound being characterized by:
- (a) having a molecular weight of less than 1000;
- (b) being an antagonist against formation of neurotoxic ADDLs from $A\beta_{1-42}$ monomers; and
- (c) exhibiting an $IC_{50}$ of about 5 µM or less in the assay of Example 1, which measures the formation of neurotoxic ADDLs.

The present invention also relates to a method a manufacturing a medicament comprising the compound as set forth in the embodiments in this section.

DETAILED DESCRIPTION OF THE INVENTION

A. Methods of the Invention

Before the methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety. Nothing herein is to be construed as an admission that the invention is not entitled to antedate such disclosure by virtue of prior invention.

The definitions used herein are limited to the application of small molecules as they relate to ADDL aggregation or oligomerization and diseases mediated by such.

This invention is directed to the discovery that the formation of soluble, oligomeric, globular, non-fibrillar, neurotoxic $A\beta_{1-42}$ peptides (ADDLs) can be antagonized by substantially pure non-peptidic compounds having a molecular weight of less than 1500, preferably less than 1000. The compounds antagonize ADDL formation at levels higher than those previously achievable.

Without being limited by any theory, it is believed that the administration of an therapeutically effective amount of one or more of the compounds described herein will interact with key assembly motifs within the $A\beta_{1-42}$ monomers or within critical motifs on the $A\beta_{1-42}$ oligomers. This interaction, in turn, will prevent the formation of neurotoxic ADDLs or the activity of such ligands. The disruption of the ADDLs or the activity of such ligands will protect long term potentiation of neuronal cells thereby obviating and/or reversing the neurotoxicity associated with ADDL. In addition, this interaction does not interfere with the formation of Aβ senile plaques.

The term "non-peptidic compound" refers to a compound, examples of which are described herein, which are not composed of peptides and/or proteins. It is understood that the presence of 1 to 10, or 1 to 5, or 1 to 2 amino acid residues attached to the compound scaffolds disclosed herein do not render such scaffolds peptidic provided that the molecular weight of the compound is less than 1500, preferably less than 1000, and the amino acid residues do not possess any antigen binding function and further provided that the scaffold itself in the absence of the amino acid residues possesses inhibition of ADDL formation as set forth in Example 1 herein. In a preferred embodiment, the non-peptidic compounds described herein contain no amino acid residues derived from one of the 20 naturally occurring amino acids.

The term "peptides" and "proteins" refer to high molecular weight compounds having a plurality of amino acid residues bound through amido (—C(O)—NR—) bonds. The amino acid residues are typically derived from one of the 20 naturally occurring amino acids.

The term "soluble" means the ability for a given substance, the solute (an example in the instant invention is the $A\beta_{1-42}$ oligomer) to dissolve in a solvent. Within the context of the instant invention, soluble Aβ oligomers are capable of being fractionated by centrifugation.

The term "oligomeric" means a protein complex of a finite number of monomer subunits. In the context of the invention, oligomers are referred to as trimers, low-n-mers, dodecamers (12-mers), and large-n-multimers composed of $A\beta_{1-42}$ peptides. The term "oligomeric" does not include senile amyloid plaques.

The term "globular" means a large soluble protein complex, which is to be distinguished from fibrils and amyloid plaques. Preferably, the globular structure ranges in size from 4 nanometers (nm) to about 12 nm, preferably, from about 4.7 to about 11 nm, which can be observed upon atomic force microscope analysis (AFM) of supernatant fractions of $A\beta_{1-42}$ soluble oligomer preparations as described in U.S. Pat. No. 6,218,506.

The term "non-fibrillar" means the $A\beta_{1-42}$ peptides and oligomeric complexes that are not aligned in a morphologically distinct pattern known as amyloid protofibrils or amyloid fibrils.

The term "ADDL" is conventionally defined as amyloid beta-derived diffusable ligands which have the following characteristics: soluble, oligomeric, globular, non-fibrillar, neurotoxic $A\beta_{1-42}$ peptides.

The term "substantially pure" is defined as substantially free of impurities, such as less than 20% impurities. In one embodiment, a compound is substantially pure if it contains less than 10% impurities and, in another embodiment, if it contains less than 1% impurities.

The compounds described herein are useful in a method for inhibiting, regulating and/or modulating assembly of ADDLs either in vitro or in vivo.

The terms "disease," "disorder," and "condition" are used inclusively and refer to any condition mediated at least in part by ADDLs. In the context of this invention the disease may be associated with insoluble amyloid fibrils, senile plaques, neurofibrillary tangles, and/or the over-expression of amyloid $\beta_{1-42}$ protein. Examples include, but are not limited to, Alzheimer's disease, Down's Syndrome, mild cognitive impairment, stroke, focal ischemia associated dementia, and neuronal degeneration. Patients amenable to treatment include individuals at risk of disease but not exhibiting symptoms, as well as patients presently exhibiting symptoms. Therefore, the compounds described herein can be administered prophylactically to the general population without the need for any assessment of the risk of the patient.

The term "patient" refers to animals, including mammals, humans, and non-human mammals. In certain embodiments, a patient is an animal, particularly an animal selected from a mammalian species including rat, rabbit, bovine, ovine, porcine, canine, feline, murine, equine, and primate, particularly human.

The methods are especially useful for individuals who have a known genetic risk of Alzheimer's disease. Such individuals include those having relatives who have been diagnosed with the disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of Alzheimer's Disease, hypercholesterolemia or atherosclerosis. Individuals presently suffering from Alzheimer's disease can be recognized from characteristic dementia, as well as the presence of risk factors described above. In addition, a number of diagnostic test are available for identifying individuals who have Alzheimer's disease. These include measurement of CSF tau and $A\beta_{1-42}$ levels. Individuals suffering from Alzheimer's disease can also be diagnosed by ADRDA criteria or the method disclosed herein.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time. Treatment can be monitored by assaying for the presence of ADDLs over time.

"Treating" or "treatment" of a disease includes: (1) preventing the disease, i.e., causing the clinical symptoms of the disease not to develop in a patient that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to a disease. A patient may also be referred to being "at risk of suffering" from a disease. This patient has not yet developed characteristic disease pathology, however are know to be predispose to the disease due to family history, being genetically predispose to developing the disease, or diagnosed with a disease or disorder that predisposes them to developing the disease to be treated.

In addition to Alzheimer's disease, several other disease are know to be associated with $A\beta_{1-42}$ formation including, but are not limited to, Down's Syndrome, stroke and mild cognitive impairment. It is conceivable that similar to Alzheimer's disease, treatment of patients suffering from or at risk of suffering from these diseases is possible due to the parallel mechanisms of the diseases.

The term "senile plaque" or "senile plaque formation" refers to the extracellular deposit of amyloid in the gray matter of the brain. The deposits are associated with degenerative neural structures. It is understood that senile plaque is different from and distinguished over ADDLs.

Similarly, over-expression of $A\beta_{1-42}$ is associated with focal ischemia associated dementia and neuronal degeneration. Over-expression of $A\beta_{1-42}$ is believed to result in accumulation of ADDLs, thereby inducing neurotoxicity. Treating a patient suffering from or at risk of suffering from one of these diseases by administration of one or more of the compounds described herein will ameliorate the neurotoxicity of over-expressed $A\beta_{1-42}$.

The term "neurotoxicity" refers to the toxic effect of ADDLs on neuronal cells either in vitro and/or in vivo. ADDLs bind to specific neuronal receptors triggering aberrant neuronal signaling, which compromises long term potentiation and causes memory deficits. Thus, ADDLs alter the function of the neuronal cell in such a manner that, while still viable, the neuron does not properly function. Such altered functionality is referred to herein as "neuronal dysfunction," which is a subclass of neurotoxicity. Persistent ADDL signaling causes aberrant transcription and the progressive loss of synapses, and very long term persistent ADDL signaling and accumulated structural pathology leads to eventual neuron death and gross brain dystrophy.

In therapeutic applications, a pharmaceutical composition containing one or more compounds described herein is administered to a patient suspected of, or already suffering from such a disease associated with the accumulation of ADDLs, wherein said compounds are administered in an amount sufficient to cure, or at least partially arrest, the symptoms of the disease (biochemical, histological and/or behavioral), including its complication and intermediate pathological phenotypes in development of the disease. In prophylactic applications, a pharmaceutical composition containing one or more compounds described herein is administered to a patient susceptible to, or otherwise at risk of, a disease associated with the accumulation of ADDLs, wherein said compounds are administered in an amount sufficient to eliminate or reduce the risk, lessen the severity, or delay the outset of the disease. This includes biochemical, histological and/or behavioral symptoms of the disease, its complications and intermediate pathological phenotypes presenting during development of the disease.

In some methods, administration of the compound reduces or eliminates mild cognitive impairment in patients that have not yet developed characteristic Alzheimer's pathology. In particular embodiments, a therapeutically effective amount intends to indicate the amount of one or more compounds described herein administered or delivered to the patient which is most likely to result in the desired response to treatment.

An "effective amount" is an amount of one or more of the compounds described herein which treats the ADDL mediated disease. Preferably, the compounds of this invention will decrease ADDL formation either in vitro or in vivo by at least 10%, 25%, 40%, 60%, 80%, 90% or 95% as compared to control.

The "therapeutically effective amount" will vary depending on the compound, the disease and its severity and the age, weight, etc., of the patient to be treated all of which is within the skill of the attending clinician. It is contemplated that a therapeutically effective amount of one or more of the compounds described herein will alter ADDL formation (including inhibiting or reversing formation of ADDLs) in the patient as compared to binding of ADDLs in the absence of treatment. As such, impairment of long term potentiation and subsequent memory formation is decreased. A therapeutically effective amount is distinguishable from an amount having a biological effect (a "biologically effective amount"). A compound of the present invention may have one or more biological effects in vitro or even in vivo, such as reduction in ADDL formation to some extent. A biological effect, however, may not result in any clinically measurable therapeutically effect as described above as determined by methods within the skill of the attending clinician.

A "neuronal cell" or "neuron" is a cell that transmits and processes signals in the brain or other parts of the nervous system. Additionally, a neuronal cell, as used in the invention, can be isolated from animal brain tissue and grown in tissue culture. The isolated cells can be comprised of an established neuronal cell line selected from for example, but are not limited to, MC65; HCN-2; SH-SY5Y; SK-N-AS; SK-N-FI; SK-N-DZ; H19-7/IGF-IR; QNR/D; QNR/K2; C8-D30; C8-S; C8-D1A; OLGA-PH-J/92; Daoy; RSC96; SW10; RT4-D6P2T; RN33B; PC-12; DBRTG-05MG; C8-B4; SK-N-SH; B35; R3[33-10ras3]; Neuro-2A; and HCN-1A or any genetic, chemical, and/or biochemical modified variants thereof. The isolated cells can also be comprised of primary cells and/or astrocytes isolated from neuronal tissues selected from, for example, but are not limited to, the hippocampus; cerebellum; cortex; hypothalamus; mid-brain; spinal cord; striatum; frontal lobe; temporal lobe; parietal lobe; occipital lobe and any genetic, chemical, and/or biochemical modified variants thereof. The isolated, cultured animal cell can be comprised of a neural stem cell or any differentiated, genetic, chemical, and/or biochemical modified variants thereof.

As used herein, the term "neuronal tissue" refers to any portion of the central nervous system including, but not limited to, the brain or spinal cord. Neuronal tissue can be composed of, at least in part, neuronal cells.

The term "amyloid fibrils" means protein aggregates sharing specific structural traits. Histopathological techniques generally identify the structures by apple-green birefringence when stained with Congo red and seen under polarized light.

The term "tangles" means the neurofibrillary tangles formed inside of degenerating neurons by bundling of paired helical filaments, which assemble from hyperphosphorylated forms of the microtubule-associated protein know as tau.

B. Compounds

The compounds useful in the methods described herein are substantially pure, non-peptidic and have a molecular weight of less than 1000. In one embodiment, the compounds useful in the methods of the invention preferably contain one or more and any combination of the following characteristics: (1) low or sub-micromolar potency when tested in the FRET assay described herein; (2) non-aggregating; (3) little or no neuronal toxicity when administered to a patient; (4) favorable solubility in an aqueous environment; (5) chemically tractable; (6) dose dependent characteristics; (7) reversibly bind to the A$\beta$ protein; (8) capable of amyloid $\beta$ monomer binding; (9) capable of binding soluble amyloid $\beta$ oligomers.

In one embodiment of the invention, the compounds useful for treating patients are suitable for oral delivery. In this embodiment, the compound are compliant with Lipinski's rule-of-five which provides a criteria to evaluate drug likeness. The rule states that, in general, an orally active drug has: no more than 5 hydrogen bond donors (OH and NH groups); no more than 10 hydrogen bond acceptors (notably N and O); a molecular weight under 500 g/mol; and a partition coefficient log P less than 5.

1. Compound Selection

A preferred method of selecting compounds for their use in the methods of the invention involves assaying the compounds with Fluorescence Resonance Energy Transfer (FRET). FRET has been used to measure, detect, identify, assay, analyze, and characterize various interactions and processes in biological systems (see e.g., Mitra et al. (1996) Gene 173:13-17; De Angelis (1999) Physiol. Genomics. 21:93-99; Latif and Graves (2000) Thyroid 10(5):407-412; Rye (2001) Methods 24(3):278-288; Kenworthy (2001) Methods 24(3): 289-296; Periasamy (2001) J. Biomed. Opt. 6(3):287-291; Truong and Ikura (2001) Curr. Opin. Struct. Biol. 11(5):573-578; Zhang et al. (2002) Nat. Rev. Mol. Cell. Biol. 3(12):906-918; Sitte and Freissmuth (2003) Eur. J. Pharmacol. 479:229-236; Milligan (2004) Eur. J. Pharm. Sci. 21(4):397-405; Herman et al. (2004) Methods Mol. Biol. 261:351-370; Roda et al. (2004) Trends Biotechnol. 22(6):295-303; Wallrabe and Periasamy (2005) Curr. Opin. Biotechnol. 16(1):19-27; Milligan and Bouvier (2005) FEBS J. 272(12):2914-2915; references in any of the foregoing; and the like).

FRET methods, protocols, techniques, assays, and the like are described generally and specifically in a number of patents and patent applications, including: U.S. Pat. No. 6,908, 769; U.S. Pat. No. 6,824,990; U.S. Pat. No. 6,762,280; U.S. Pat. No. 6,689,574; U.S. Pat. No. 6,661,909; U.S. Pat. No. 6,642,001; U.S. Pat. No. 6,639,078; U.S. Pat. No. 6,472,156; U.S. Pat. No. 6,456,734; U.S. Pat. No. 6,376,257; U.S. Pat. No. 6,348,322; U.S. Pat. No. 6,323,039; U.S. Pat. No. 6,291, 201; U.S. Pat. No. 6,280,981; U.S. Pat. No. 5,914,245; U.S. Pat. No. 5,661,035; references in any of the foregoing; and the like.

Similarly, fluorescence polarization (FP) has also been used to measure, detect, identify, assay, analyze, and characterize various interactions and processes in biological systems (see e.g., Lundblad et al. (1996) Mol. Endocrinol. 10(6): 607-612; Nasir and Jolley (1999) Comb. Chem. High Throughput Screen. 2(4): 177-190; Park and Raines (2004) Methods Mol. Biol. 261:161-166; references in any of the foregoing; and the like).

Fluorescence polarization (FP) methods, protocols, techniques, assays, and the like are described generally and specifically in a number of patents and patent applications, including: U.S. Pat. No. 6,794,158; U.S. Pat. No. 6,632,613; U.S. Pat. Nos. 6,630,295; 6,596,546; U.S. Pat. Nos. 6,569,628; 6,555,326; U.S. Pat. No. 6,511,815; U.S. Pat. No. 6,448,018; U.S. Pat. No. 6,432,632; U.S. Pat. No. 6,331,392; U.S. Pat. No. 6,326,142; U.S. Pat. No. 6,284,544; U.S. Pat. No. 6,207,397; U.S. Pat. No. 6,171,807; U.S. Pat. No. 6,066,505; U.S. Pat. No. 5,976,820; U.S. Pat. No. 5,804,395; U.S. Pat. No. 5,756,292; U.S. Pat. No. 5,445,935; U.S. Pat. No. 5,427,960; U.S. Pat. No. 5,407,834; U.S. Pat. No. 5,391,740; U.S. Pat. No. 5,315,015; U.S. Pat. No. 5,206,179; U.S. Pat. No. 5,070,025; U.S. Pat. No. 5,066,426; U.S. Pat. No. 4,952,691; U.S. Pat. No. 4,863,876; U.S. Pat. No. 4,751,190; U.S. Pat. No. 4,681,859; U.S. Pat. No. 4,668,640; U.S. Pat. No. 4,614,823; U.S. Pat. No. 4,585,862; U.S. Pat. No. 4,510,251; U.S. Pat. No. 4,476,229; U.S. Pat. No. 4,429,230; U.S. Pat. No. 4,420,568; U.S. Pat. No. 4,203,670; references in any of the foregoing; and the like.

FRET and FP have been used in the field of amyloid research (see e.g., U.S. Pat. No. 6,927,401; U.S. Pat. No. 6,906,104; U.S. Pat. No. 6,905,827; U.S. Pat. No. 6,881,546; U.S. Pat. No. 6,864,290; U.S. Pat. No. 6,864,103; U.S. Pat. No. 6,858,383; U.S. Pat. No. 6,846,813; U.S. Pat. No. 6,828,106; U.S. Pat. No. 6,803,188; U.S. Pat. No. 6,770,448; U.S. Pat. No. 6,713,276; U.S. Pat. No. 6,600,017; U.S. Pat. No. 6,515,113; U.S. Pat. No. 6,495,664; U.S. Pat. No. 6,323,039; U.S. Pat. No. 6,294,330; U.S. Pat. No. 6,280,981; U.S. Pat. No. 6,197,928; U.S. Pat. No. 5,981,200; Kim and Lee (2004) Biochem. Biophys. Res. Commun. 316(2):393-397; Bacskai et al. (2003) J. Biomed. Opt. 8(3):368-375; Gorman, P. M. et al. (2003) J. Mol. Biol. 325(4):743-757; Garzon-Rodrequez et al. (1997) J. Biol. Chem. 272(34):21037-21044; Lindgren et al. (2005) Biophys. J. 88(6):4200-4212; Lewis et al. (2004) Neurobiol. Aging 25(9):1175-1185; Leissring et al. (2003) J. Biol. Chem. 278(39):37314-37320; Taylor et al. (2003) J. Protein Chem. 22(1):31-40; Allsop et al. (2001) Biochem. Soc. Symp. 67:1-14; Allsop et al. (2001) Biochem. Biophys. Res. Commun. 285(1):58-63; Huang et al. (2000) J. Biol. Chem. 275(46):36436-36440; references in any of the foregoing; and the like).

2. Applications of FRET for Compound Discovery

The FRET assay of Example 1 was used on a variety of commercially available compound libraries to assess the specific inhibition formation of soluble amyloid $\beta_{1-42}$ oligomers of each compound. Lead compounds were identified and further compound libraries were obtained. In addition, structure activity relationships around lead compounds were conducted leading to still further enhancements in activity.

3. Exemplary Compounds Useful in the Methods of the Invention

Certain examples of compounds useful in this invention are presented below in Table 1 below. It is to be understood that the illustration of these compounds is in no way limiting the invention to the compounds described in these tables and it is therefore contemplated that other compounds are suitable for use in this invention.

Also provided in the table are the compounds $IC_{50}$ values as tested using the assay described in Example 1. In each case, the compounds recited either were commercially available from the source indicated in the table. It should also be noted that the following compounds may exhibit stereoisomerism (i.e., E and Z isomers) and the invention contemplates use of either isomer and mixtures thereof.

TABLE 1

Exemplary Compounds

| No. | Compound Structure | Compound Name | $IC_{50}$ (μM) | Source |
|---|---|---|---|---|
| 1. | | N-(2-Methoxy-phenyl)-2-oxo-2-{N'-[3-oxo-3-thiophen-2-yl-1-trifluoromethyl-prop-(Z)-ylidene]-hydrazino}-acetamide | 3.9 | deCODE |
| 2. | | 2-{[1-(2-Hydroxy-3-methoxy-phenyl)-meth-(E)-ylidene-hydrazinooxalyl]-amino}-6-methyl-4,5,6,7-tetrahydro-benzo[b]thiophene-3-carboxylic acid ethyl ester | 3.5 | Aldrich |

TABLE 1-continued

Exemplary Compounds

| No. | Compound Structure | Compound Name | IC$_{50}$ (μM) | Source |
|---|---|---|---|---|
| 3. | | 2-{[1-(2-Hydroxynaphthalen-1-yl)-meth-(E)-ylidene-hydrazinooxalyl]-amino}-6-methyl-4,5,6,7-tetrahydro-benzo[b]thiophene-3-carboxylic acid ethyl ester | 4.4 | Aldrich |
| 4. | | 2-{[1-(2-Hydroxyphenyl)-meth-(E)-ylidene-hydrazinooxalyl]-amino}-6-methyl-4,5,6,7-tetrahydro-benzo[b]thiophene-3-carboxylic acid ethyl ester | 1.1 | Aldrich |
| 5. | | 2-(5-hydroxy-3-isobutyl-5-(trifluoromethyl)-4,5-dihydro-1H-pyrazol-1-yl)-N-(2-methoxyphenyl)-2-oxoacetamide | 3.2 | ChemDiv |
| 6. | | (E)-2-hydroxy-N'-((1-hydroxynaphthalen-2-yl)methylene)benzohydrazide | 3.8 | deCODE |

C. Testing and Administration

Effective doses of the compositions of the present invention, for the treatment of the above described diseases, vary depending upon may different factors, including means of administration, physiological state of the patient, whether the patient is human or an animal, other medications administered, and whether treatment is prophylactic or therapeutic. Usually, the patient is a human, but in certain embodiments, a patient is an animal, particularly an animal selected from a mammalian species including rat, rabbit, bovine, ovine, porcine, canine, feline, murine, equine, and primate.

The compounds can be administered on multiple occasions, wherein intervals between single dosages can be daily, weekly, monthly, or yearly. Intervals can also be irregular as indicated by measuring blood levels of Aβ$_{1-42}$ protein or ADDLs, or ADDL complexes in the patient. Alternatively, one or more of the compounds of the invention can be administered as a sustained-release formulation, in which case less frequent administration is required. Dosage and frequency may vary depending on the half-life of the compounds of the invention. In therapeutic applications, a relatively high dosage at relatively short intervals is sometimes required until progression of the disease is reduced or terminated, and preferably until the patient shows partial or complete amelioration of symptoms of the disease. Thereafter, the patient can be administered a prophylactic regime.

Administration of a pharmaceutical composition of on the compounds described herein can be carried out via a variety of routes including, but are not limited to, oral, topical, pulmonary, rectal, subcutaneous, intradermal, intranasal, intracranial, intramuscular, intraocular, or intra-articular injection and the like. The most typical route of administration is oral, although other routes can be equally effective.

One or more compounds described herein can optionally be administered in combination with other biological or chemical agents that are at least partly effective in treatment of a Aβ$_{1-42}$ associated disease. An example of such an agent is, but are not limited to, Aβ$_{1-42}$ targeted antibodies as described in International Application Nos.: WO 2003/253673; WO 2006/014478, U.S. Pat. No. 2,489,195, US Publication No. 2007-0048312, and U.S. application Ser. No. 11/571,532, which are incorporated herein by reference.

The compounds described herein may be administered to a patient in an amount sufficient to inhibit, regulate and/or modulate the formation of neurotoxic ADDLs or the activity of such ligands in said patient. A skilled clinician would be able to readily ascertain appropriate amounts of the compounds described here to effectively inhibit, regulate and/or modulate the formation of neurotoxic ADDLs or the activity of such ligands in said patient. Contemplated amounts of the compounds described herein include for example, but are not limited to, from about 0.05 to 2000 mg/m$^2$/day of one compound or more than one compound.

As noted above, the compounds described herein may be administered for example, but are not limited to, orally, topically, pulmonaryly, rectally, subcutaneously, intradermally, intranasally, intracranially, intramuscularly, intraocularly, or intra-arterially and the like. The carrier or excipient or excipient mixture can be a solvent or a dispersive medium containing for example, but are not limited to, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Moreover, other or supplementary active ingredients can also be incorporated into the final composition.

Diseases which are treated by the methods described herein include Alzheimer's disease, Down's syndrome, stroke, mild cognitive impairment, focal ischemia associated dementia and neuronal degeneration.

D. Pharmaceutical Formulations and Routes of Administration

When employed as pharmaceuticals, the compounds of this invention are usually administered in the form of pharmaceutical compositions. These compounds can be administered by a variety of routes including oral, topical, pulmonary, rectal, subcutaneous, intradermal, intranasal, intracranial, intramuscular, intraocular, or intra-articular injection. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to patient. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: ethylene diamine tetraacetic acid (EDTA), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer:drug (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

One useful buffer in the invention is sodium citrate/citric acid in the range of 5 to 50 mg per mL of sodium citrate to 1 to 15 mg per mL of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/mL, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions can be formulated in an oral unit dosage form. The term "unit dosage forms" refers to physically discrete units suitable as unitary dosages for a patient, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.05 to about 2000 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the contemplated pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |

-continued

| Ingredient | Quantity (mg/tablet) |
|---|---|
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.s. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
|---|---|
| Active Ingredient | 5.0 mg |
| Corn Oil | 1.0 mL |

Formulation Example 10

An intravenous formulation may be prepared as follows:

| Ingredient | Quantity |
|---|---|
| Active Ingredient | 250 mg |
| Isotonic saline | 1000 mL |

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Figure 1:
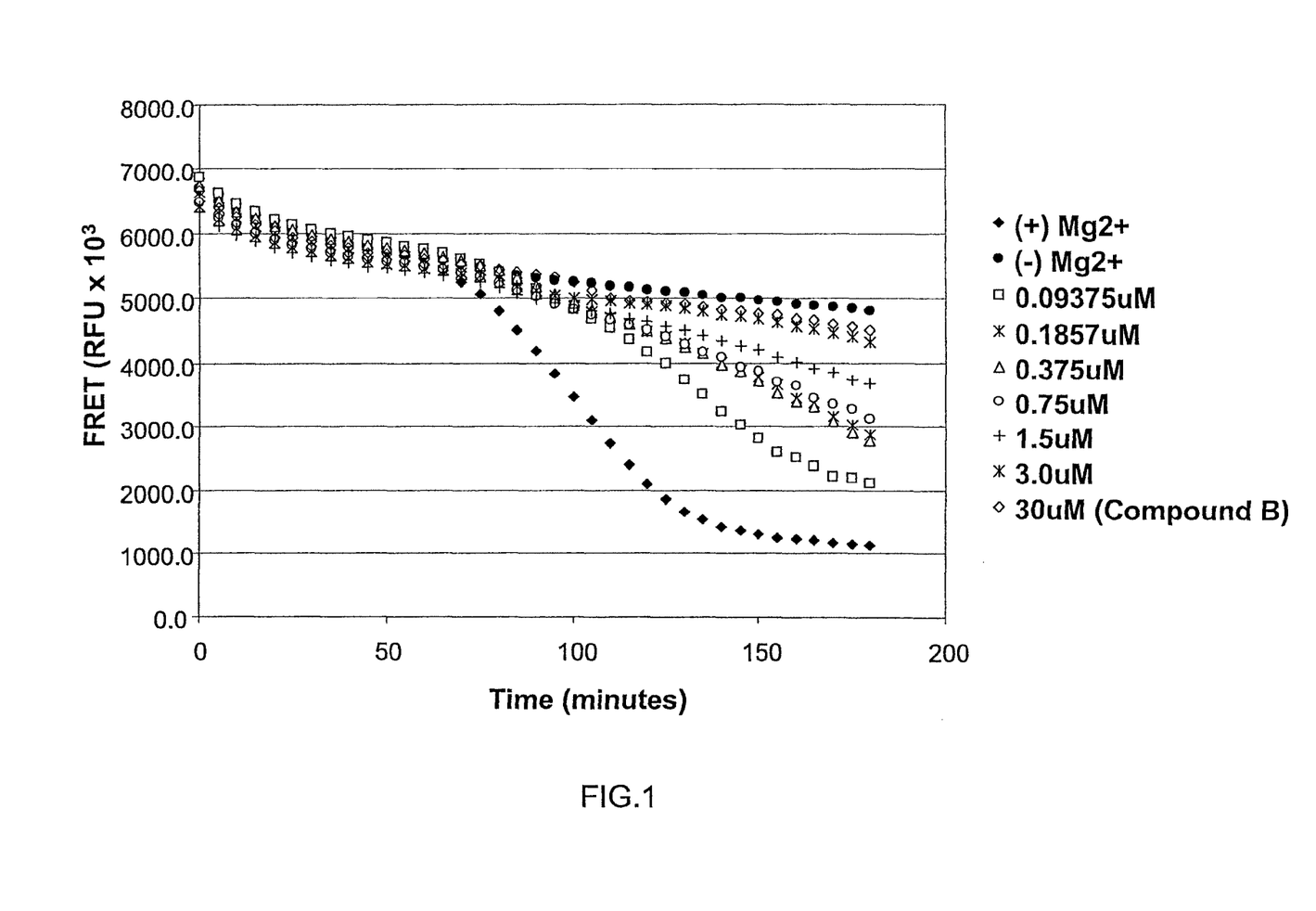
FIG. 1 shows representative dose dependent assembly inhibition of compounds described herein using FRET analysis. The results of Test Compound A assayed at concentrations between 0.05 to 3 µM are shown as well as the results of Test Compound B assayed at a concentration of 30 µM. The positive and negative controls are also shown. The X axes indicates time in minutes, where as the Y axes indicates the relative fluorescence units (RFU)×$10^3$ measured by the FRET assay in Example 1.

Indirect techniques, usually involve formulating the compositions to provide for drug latentiation by the conversion of hydrophilic drugs into lipid-soluble drugs. Latentiation is generally achieved through blocking of the hydroxyl, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The following examples are offered to illustrate this invention and are not to be construed in any way as limiting the scope of this invention. Unless otherwise stated, all temperatures are in degrees Celsius.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In these examples and elsewhere, abbreviations have the following meanings:

μL or μl=Microliter
DMSO=dimethylsulfoxide
g=Gram
h=Hour
Hz=Hertz
M=Molar
mg=Milligram
min=Minute
mL=Milliliter
mM=Millimolar
mm=Millimeter
mmol=Millimolar
mol=Moles
MS=Mass Spectroscopy
N=Normal
nm=Nanometer
μM=Micromolar

Example 1

FRET Assay

Fluorescence (or Förster) Resonance Energy Transfer (FRET) is a distance-dependent, non-radiative transfer of energy in which the de-excitation of one fluorophore (donor) is coupled to excitation of another fluorophore (acceptor). FRET occurs if (1) the quantum of energy emitted by a donor fluorophore corresponds to an acceptor fluorophore's excitation energy, (2) the orientations of donor and acceptor transition dipoles are nearly parallel and (3) the donor fluorescent emission spectrum overlaps the acceptor absorption spectrum.

In this assay, assembly of $A\beta_{1-42}$ oligomer formation is monitored by FRET using N-terminal conjugates of fluorescein-$A\beta_{1-42}$ as both the donor and acceptor fluorophore (fluorescein-fluorescein $R_o$~45 Å). $A\beta_{1-42}$ monomers assembling into oligomeric species results in a decrease of fluorescence as the fluorescein labeled $A\beta_{1-42}$ peptides become proximal to each other and FRET efficiency increases. Inhibition of $A\beta_{1-42}$ assembly is observed as the absence or attenuation of fluorescein quenching.

FRET and FP assays are performed in 384-well Corning Non-Binding Surface, black, opaque microtiter plates, and the assay buffer consists of 50 mM MOPS-Tris (pH 8.0) with 100 mM $MgCl_2$. The assay volume, containing 0.2 μM FITC-Aβ(1-42) and 0.8 μM Aβ(1-42), is 50 μl and the temperature is 37° C. ADDL assembly is monitored on a Tecan GENios Pro plate reader, exciting at a wavelength of 485 nm and detecting emission at a wavelength of 515 nm. Kinetic traces are collected by recording fluorescence intensity and polarization readings every five minutes over about a three to about a six-hour time course. Negative control reactions, which do not appreciably assemble into ADDLs during this time, lack $MgCl_2$ but contain all other buffer and peptide components. Positive control reactions contain all buffer components in the absence of added small molecule or antibody reagents. To test for ADDL assembly inhibition, the non-peptidic compound was incubated with the peptide mixture at six concentrations from about 30 μM decreasing to about 0.05 μM.

Using the above described assay with the conditions of: the Test Compound A ranging from 0.05 to 3 mM, Test Compound A shows dose dependent inhibition of $A\beta_{1-42}$ oligomer assembly as shown in FIG. 1. Test Compound A appears as compound 4 of Table 1. Additionally, Test Compound B assayed at a concentration of 30 μM shows only partial assembly inhibition at very high concentrations (FIG. 1). Examples of other compounds having a molecular weight of less than 1000 and requisite activity as tested in this assay are found in Table 1.

Example 2

Comparative Example of Putative Aβ Assembly Blocker

Figure 2:
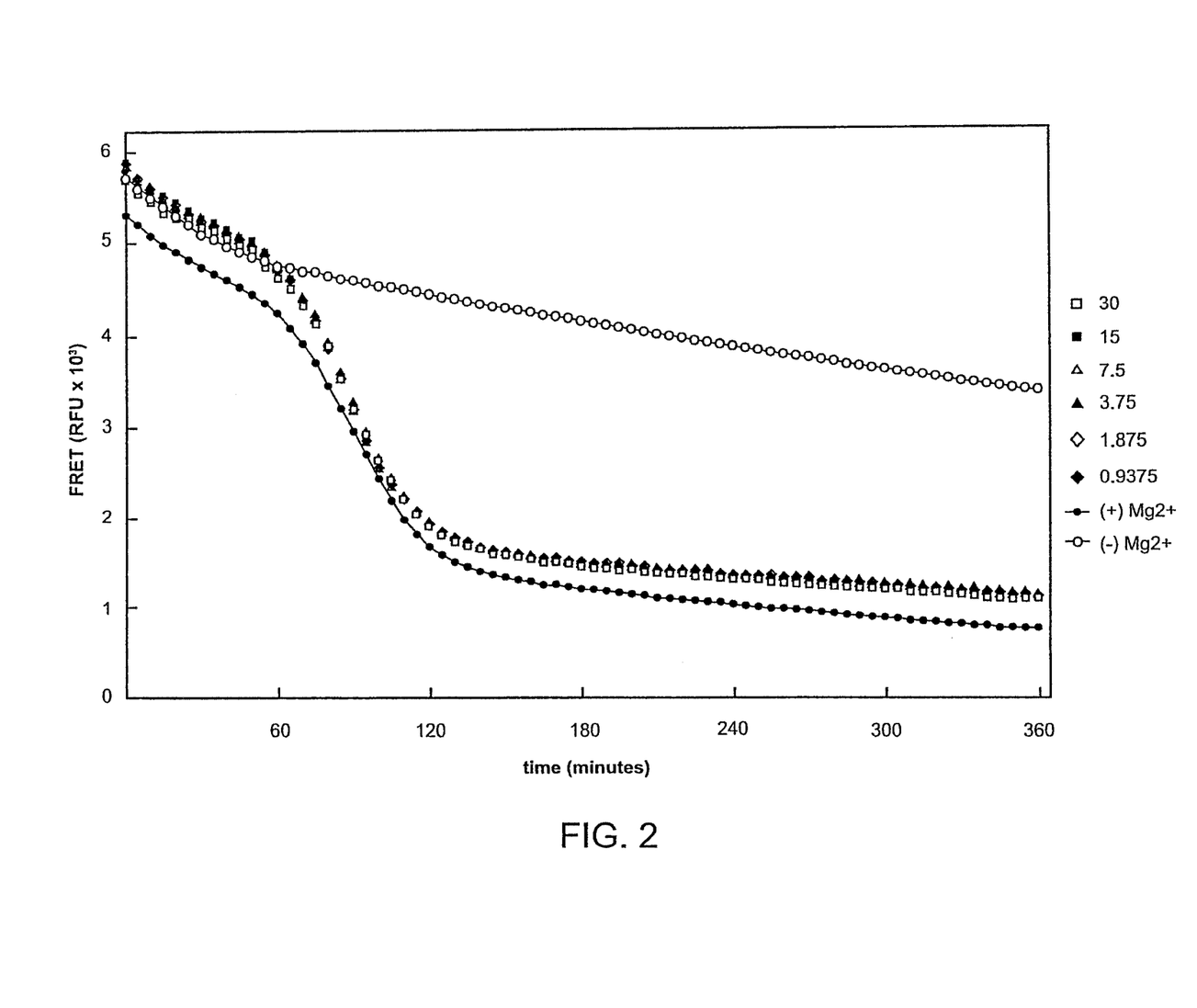
FIG. 2 shows representative dose dependent assembly inhibition of the putative amyloid fibril blocker compound Alzhemed™ (Neurochem) tested in the FRET assay described herein. The positive and negative controls are also shown. The X axes indicates time in minutes, where as the Y axes indicates the relative fluorescence units (RFU)×$10^3$ measured by the FRET assay.

Using the FRET assay described above, several compounds originally developed as amyloid fibril blockers were tested for blocking of $A\beta_{1-42}$ monomer assembly into Aβ oligomers. The compounds tested include, Alzhemed™ (Neurochem), scyllo-inositol also know as AZD-103 (Ellipsis), SP-235 (Samaritan), benzofarans (GE), 9-acridinones (Warner-Lambert), cyclodextrins (University of Illinois, Chicago), RS-406 (Sankyo), Clioquinol (Prana), and Curcumin (UCLA/UCI). Standard FRET assay conditions described in Example 1 were used. The inability of the compound Alzhemed to inhibit $A\beta_{1-42}$ monomer assembly into Aβ oligomers is shown in FIG. 2. These results are representative of all the compounds listed above, which were originally developed as amyloid fibril blockers.

Example 3

Alternating Lever Cyclic Ratio Rat Model

Preparations of $A\beta_{1-42}$ ADDLs and a potential therapeutic compound under the Alternating Lever Cyclic Ratio (ALCR) rat model of AD are tested to show in vivo efficacy. This highly sensitive model has been able to detect cognitive deficits due to direct injection of cell-derived Aβ oligomers into rat brain. Using this technique, a direct injection of ADDLs made from synthetic $A\beta_{1-42}$ and a putative therapeutic compound under the ALCR procedure may be tested.

The ALCR test has proven to be much more sensitive than previously published methods for measuring drug effects on cognitive function. In this task, rats must learn a complex sequence of lever-pressing requirements in order to earn food reinforcement in a two-lever experimental chamber. Subjects must alternate between two levers by switching to the other lever after pressing the first lever enough to get food reward. The exact number of presses required for each food reward changes, first increasing from 2 responses per food pellet up to 56 presses per food pellet, then decreasing back to 2 responses per pellet. Intermediate values are based on the quadratic function, $x^2-x$. One cycle is an entire ascending and descending sequence of these lever press requirements (e.g., 2, 6, 12, 20, 30, 42, 56, 56, 42, 30, 20, 12, 6, and 2 presses per food reward). Six such full cycles are presented during each daily session. Errors are scored when the subject perseveres on a lever after pressing enough to get the food reward, i.e., does not alternate (a Perseveration Error), or when a subject switches levers before completing the response requirement on that lever (an Approach Error).

Materials and Methods

Synthetic $A\beta_{1-42}$ powder is dissolved in 1,1,1,3,3,3 hexafluoroisopropanol (HFIP) to afford a solution of $A\beta_{1-42}$ in HFIP of about 1 mM and allowed to incubate at ambient temperature for about 1 h. The resulting solution is chilled on ice for about 5-10 min, then aliquoted into eppendorf tubes to provide about 50 μL of solution per tube. The tubes are then placed in a chemical fume hood and allowed to stand overnight to allow the HFIP to evaporate under a slow stream of nitrogen. To remove final traces of HFIP, the tubes are subjected to two SpeedVac cycles of 15 min at room temperature and about 15 to 25 mm Hg of vacuum. The resulting films of monomerized $A\beta_{1-42}$ peptide are stored over desiccant at −80° C. until used.

A tube of monomerized $A\beta_{1-42}$ peptide is warmed to room temperature and the $A\beta_{1-42}$ peptide is dissolved in anhydrous DMSO to afford a peptide stock DMSO solution containing about 10 μM to about 100 μM $A\beta_{1-42}$ peptide in DMSO.

2 μL of a 20 mM stock solution of test compound in anhydrous DMSO is added to about 998 μL of neural basal media (phenol red free, Gibco 12348-017) to give a compound neural basal media solution containing 40 μM of test compound in neural basal media.

For the $A\beta_{1-42}$ peptide only treatment, peptide stock DMSO solution is added to 37° C. neural basal to obtain the requisite $A\beta_{1-42}$ peptide monomer concentration, provided that the maximum concentration of DMSO is 1% or less, and the tube is vortexed for 30 to 60 seconds, spun down briefly in a microfuge and incubated at 37° C. for 15 min prior to the start of injections.

For the $A\beta_{1-42}$ peptide plus test compound treatment, peptide stock DMSO solution is added to 37° C. compound neural basal media solution to obtain the requisite $A\beta_{1-42}$ peptide monomer concentration, provided that the maximum concentration of DMSO is 1% or less, and the tube is vortexed for 30 to 36 seconds, spun down briefly in a microfuge and incubated at 37° C. for 15 min prior to the start of injections.

For control injections, compound neural basal media solution is incubated at 37° C. for 15 min prior to the start of injections.

Rats: Rats are trained under ALCR until their error rates are stable. Once the rats are placed upon the final ALCR procedure, training sessions are conducted 7 days each week until the end of the study.

Surgery: All rats receive a single 28 ga cannula, which is permanently affixed to the skull, and aimed at the lateral ventricle. Half the rats receive cannula in the right ventricle and half receive cannula in the left ventricle. Rats are allowed 5 days to recover from surgery before training resumed.

Injection of Test Material and ALCR Testing: Test are conducted about every fourth day. Animals received a 20 μL injection of control, peptide, or peptide plus compound solutions via the implanted cannula over about 3 to 4 minutes. Animals are tested about 3 hours following injection.

Error Rate Analysis: All error rates under will be compared to baseline error rates consisting of at least 3 non-treatment days temporally contiguous to the injection. Student's T test of statistical inference was used for analysis of effects.

Contemplated Results

It is contemplated that a significant increase in Perseveration Error rate will be found between baseline error rates and error rates produced by $A\beta_{1-42}$ ADDLs. It is also contemplated that addition of one or more of the compounds described herein will not increase error rates when given alone, but when combined with the $A\beta_{1-42}$ ADDLs, the compound(s) will eliminate the increase in Perseveration Errors. Thus, it is contemplated that at least one or more of the compounds described herein will rescued errors produced by $A\beta_{1-42}$ ADDLs.

From the foregoing description, various modifications and changes in the compositions and methods will occur to those skilled in the art. All such modifications coming within the scope of the appended claims are intended to be included therein.

What is claimed is:

1. A method for antagonizing neurotoxic ADDL formation from monomeric $A\beta_{1-42}$ by contacting monomeric $A\beta_{1-42}$ with an effective amount of a compound selected from the group consisting of N-(2-Methoxy-phenyl)-2-oxo-2-{N'-[3-oxo-3-thiophen-2-yl-1-trifluoromethyl-prop-(Z)-ylidene]-hydrazino}-acetamide, 2-{[1-(2-Hydroxy-3-methoxy-phenyl)-meth-(E)-ylidene-hydrazinooxalyl]-amino}-6-methyl-4,5,6,7-tetrahydro-benzo[b]thiophene-3-carboxylic acid ethyl ester, 2-{[1-(2-Hydroxynaphthalen-1-yl)-meth-(E)-ylidene-hydrazinooxalyl]-amino}-6-methyl-4,5,6,7-tetrahydro-benzo[b]thiophene-3-carboxylic acid ethyl ester, 2-{[1-(2-Hydroxyphenyl)-meth-(E)-ylidene-hydrazinooxalyl]-amino}-6-methyl-4,5,6,7-tetrahydro-benzo[b]thiophene-3-carboxylic acid ethyl ester, 2-(5-hydroxy-3-isobutyl-5-(trifluoromethyl)-4,5-dihydro-1H-pyrazol-1-yl)-N-(2-methoxyphenyl)-2-oxoacetamide, (E)-2-hydroxy-N'-((1-hydroxynaphthalen-2-yl)methylene)benzohydrazide, or a stereoisomer thereof or a mixture of the stereoisomers, or a pharmaceutical salt of the compound, stereoisomer or mixture.

2. The method of claim 1, wherein the compound is N-(2-Methoxy-phenyl)-2-oxo-2-{N'-[3-oxo-3-thiophen-2-yl-1-trifluoromethyl-prop-(Z)-ylidene]-hydrazino}-acetamide, or a stereoisomer thereof or a mixture of the stereoisomers, or a pharmaceutical salt of the compound, stereoisomer or mixture.

3. The method of claim 1, wherein the compound is 2-{[1-(2-Hydroxy-3-methoxy-phenyl)-meth-(E)-ylidene-hydrazinooxalyl]-amino}-6-methyl-4,5,6,7-tetrahydro-benzo[b]thiophene-3-carboxylic acid ethyl ester, or a stereoisomer thereof or a mixture of the stereoisomers, or a pharmaceutical salt of the compound, stereoisomer or mixture.

4. The method of claim 1, wherein the compound is N-(2-Methoxy-phenyl)-2-{[1-(2-Hydroxynaphthalen-1-yl)-meth-(E)-ylidene-hydrazinooxalyl]-amino}-6-methyl-4,5,6,7-tetrahydro-benzo[b]thiophene-3-carboxylic acid ethyl ester, or a stereoisomer thereof or a mixture of the stereoisomers, or a pharmaceutical salt of the compound, stereoisomer or mixture.

5. The method of claim 1, wherein the compound is N-(2-Methoxy-phenyl)-2-{[1-(2-Hydroxyphenyl)-meth-(E)-ylidene-hydrazinooxalyl]-amino}-6-methyl-4,5,6,7-tetrahydro-benzo[b]thiophene-3-carboxylic acid ethyl ester, or a stereoisomer thereof or a mixture of the stereoisomers, or a pharmaceutical salt of the compound, stereoisomer or mixture.

6. The method of claim 1, wherein the compound is N-(2-Methoxy-phenyl)-2-(5-hydroxy-3-isobutyl-5-(trifluoromethyl)-4,5-dihydro-1H-pyrazol-1-yl)-N-(2-methoxyphenyl)-2-oxoacetamide, or a stereoisomer thereof or a mixture of the stereoisomers, or a pharmaceutical salt of the compound, stereoisomer or mixture.

7. The method of claim 1, wherein the compound is N-(2-Methoxy-phenyl)-(E)-2-hydroxy-N-((1-hydroxynaphthalen-2-yl)methylene)benzohydrazide, or a stereoisomer thereof or a mixture of the stereoisomers, or a pharmaceutical salt of the compound, stereoisomer or mixture.

* * * * *